(12) United States Patent
Puppels et al.

(10) Patent No.: US 7,499,153 B2
(45) Date of Patent: Mar. 3, 2009

(54) USE OF HIGH WAVENUMBER RAMAN SPECTROSCOPY FOR MEASURING TISSUE

(75) Inventors: Gerwin Jan Puppels, Rotterdam (NL); Rolf Wolthuis, Rotterdam (NL); Senada Koljenovic, Rotterdam (NL)

(73) Assignee: River Diagnostics B.V., Rotterdam (NL)

( * ) Notice: Subject to any disclaimer, the term of this patent is extended or adjusted under 35 U.S.C. 154(b) by 398 days.

(21) Appl. No.: 10/537,074

(22) PCT Filed: Dec. 2, 2003

(86) PCT No.: PCT/NL03/00815

§ 371 (c)(1),
(2), (4) Date: Feb. 21, 2006

(87) PCT Pub. No.: WO2004/051242

PCT Pub. Date: Jun. 17, 2004

(65) Prior Publication Data

US 2006/0139633 A1     Jun. 29, 2006

(30) Foreign Application Priority Data

Dec. 2, 2002   (EP) .................................. 02080032

(51) Int. Cl.
*G01J 3/44*      (2006.01)
*G01N 21/64*   (2006.01)
*G01N 21/65*   (2006.01)

(52) U.S. Cl. ...................... 356/73; 356/301; 356/318; 356/417; 250/461.1

(58) Field of Classification Search .................. 356/301
See application file for complete search history.

(56) References Cited

U.S. PATENT DOCUMENTS 5,304,173 A     4/1994   Kittrell et al.

(Continued)

FOREIGN PATENT DOCUMENTS

WO     WO 98 41849 A1     9/1998
WO     WO 01 33189 A2     5/2001

OTHER PUBLICATIONS

International Search Report of PCT/NL03/00815; Feb. 25, 2004.

(Continued)

*Primary Examiner*—F. L Evans
(74) *Attorney, Agent, or Firm*—K&L Gates LLP

(57) ABSTRACT

The invention is related to the instrument for measuring a Raman signal of tissue, the instrument comprising a laser, a signal detection unit for measuring the Raman signal, and a fiber optic probe, wherein the fiber optic probe comprises one or more optical fibers for directing laser light onto the tissue and for collecting light that is scattered by the tissue and guiding the collected light away from the tissue towards the signal detection unit, wherein the fiber or fibers for collecting light have substantially no Raman signal in one or more parts of the 2500-3700 cm$^{-1}$ spectral region, and wherein the detection unit records the Raman signal scattered by the tissue in said spectral region. The invention enables ex vivo, in vitro and in vivo analysis and diagnosis of atherosclerotic plaque and detection of tumor tissue with great advantages over current state-of-the-art technology.

16 Claims, 8 Drawing Sheets

U.S. PATENT DOCUMENTS

| | | |
|---|---|---|
| 5,621,522 A | 4/1997 | Ewing et al. |
| 5,652,653 A | 7/1997 | Alsmeyer et al. |
| 5,864,397 A | 1/1999 | Vo-Dinh |
| 5,911,017 A | 6/1999 | Wach et al. |
| 6,205,272 B1 | 3/2001 | O'Rourke et al. |
| 2001/0012429 A1 | 8/2001 | Wach et al. |

OTHER PUBLICATIONS

S.D. Schwab and R.L. McCreery, "Versatile, Efficient Raman Sampling with Fiber Optics", Analytical Chemistry, 1984, pp. 2199-2204, vol. 56.

M.L. Myrick et al., "Comparison of Some Fiber Optic Configurations For Measurement of Luminescence and Raman Scattering", Applied Optics, Mar. 20, 1990, pp. 1333-1334, vol. 29.

Cholesterol
R=0.95

Cholesteryl
esters
R=0.93 triglycerides
R=0.96

Raman map adjacent section, H&E stained

K-means pseudo-color Raman map adjacent section, H&E stained

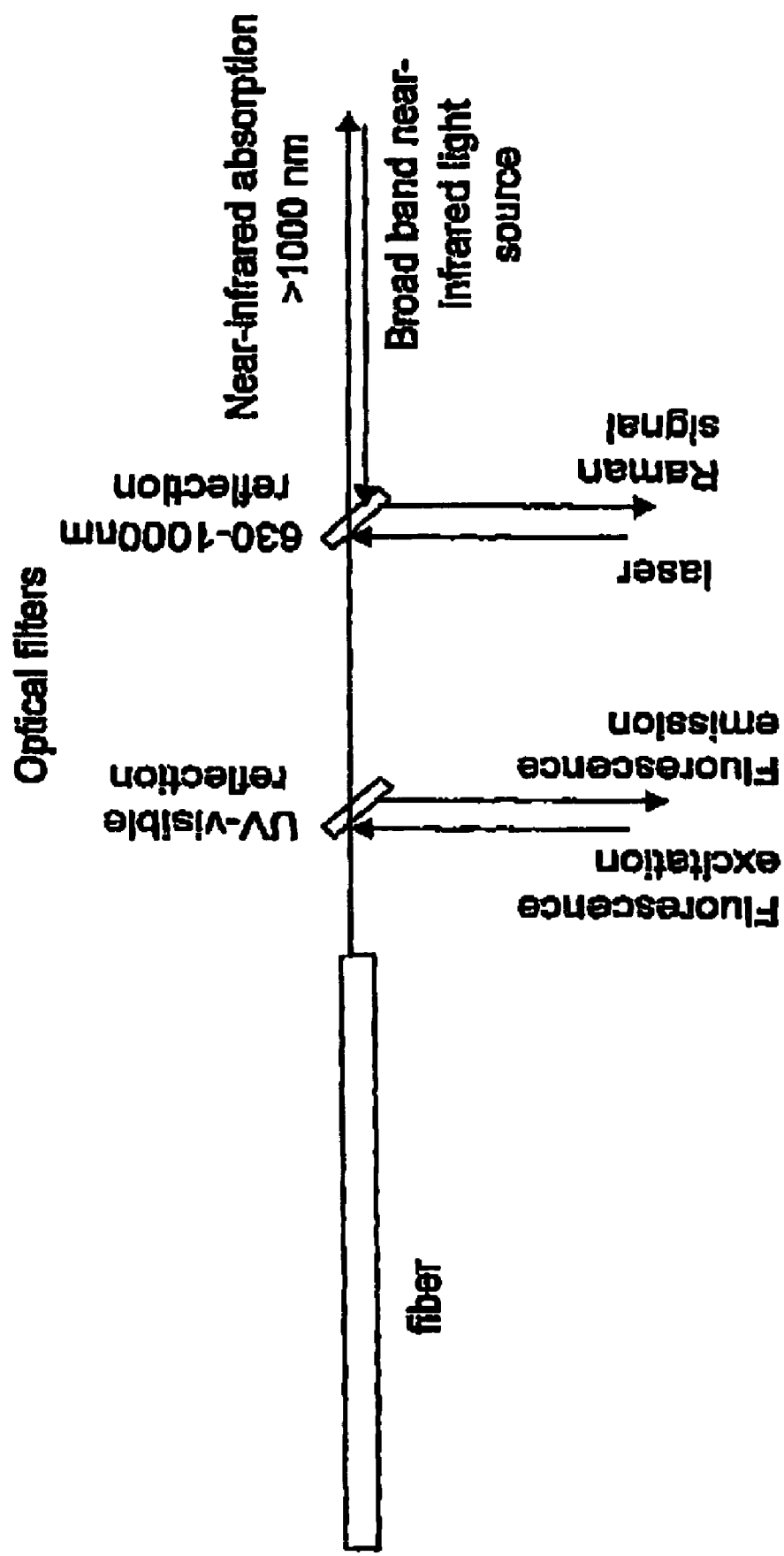

USE OF HIGH WAVENUMBER RAMAN SPECTROSCOPY FOR MEASURING TISSUE

FIELD OF INVENTION

This Invention relates to an instrument and the use thereof for measuring a Raman signal of a tissue, comprising a laser, a signal detection unit, and a fiber optic probe.

BACKGROUND OF INVENTION

Atherosclerosis is an important cause of death in many parts of the world. Therefore, many techniques have been developed to obtain information about the plaque that develops in blood vessels. Image techniques such as angiography, magnetic resonance imaging, intravascular ultrasound, and optical coherence tomography provide information regarding the location of a plaque or blood vessel obstruction and about the morphology or internal structure of the plaque. However, they do not enable detailed in vivo analysis of the molecular composition of the plaque. Knowledge of the molecular composition of a plaque is important e.g. for determining the risk of acute cardiac events. So-called stable plaque and vulnerable plaque are distinguished, where it is thought that the vulnerable plaque can give rise to such acute, often fatal events. Such an event is triggered by rupturing of the thin fibrous cap of the plaque, bringing the contents of the lipid pool of the plaque into contact with the blood stream, leading to thrombogenesis and occlusion of the artery.

Fluorescence based methods have been shown to be able to distinguish between normal artery wall and atherosclerotic plaque in vitro. However fluorescence spectra are easily disturbed by light absorbing molecules in the tissue and in blood, limiting its applicability.

Of all methods to obtain information about atherosclerotic plaque composition and which can in principle be applied in vivo, intravascular Raman spectroscopy provides the most detailed information. In Raman spectroscopy, the Stokes-shift between light that is incident on a sample that is investigated and the light that is in elastically scattered by the sample is expressed in relative wavenumbers ($\Delta cm^{-1}=(1/\lambda_{in}-1/\lambda_{scattered})10^{-2}$ with $\lambda$ (wavelength) in meter). The wavenumber region between about 400 and 2000 $cm^{-1}$ of the Raman spectrum (the so-called fingerprint region) is used to obtain this information. This region of the spectrum contains many bands that can be discerned and which individually and/or in combinations can be used to obtain information about the molecular composition of the tissue.

Studies in the field of atherosclerosis are only related to the fingerprint region, since this spectral region is very informative for analysis or diagnosis. Examples of such studies an e.g. found in the papers of H. P. Buschman, E. T. Marple, M. L. Wach, B. Bennett, T. C. Schut, H. A. Bruining, A. V. Bruschke, A. van der Laarse. and G. J. Puppels, Anal. Chem. 72 (2000), 3771-3775, which discusses the in vivo determination of the molecular composition of artery wall by intravascular Raman spectroscopy, using a multifiber probe and measuring in the 400-1800 $cm^{-1}$ region; R. H. Clarke, E. B. Hanlon, J. M. Isner, H. Brody, Appl. Optics 26 (1917), 3175-3177, which discusses laser Raman spectroscopy of calcified atherosclerotic lesions in cardiovascular tissue, also in the fingerprint region; and J. F. Brennan T. J. Romer, R. S. Lees, A. M. Tercyak, J. R. Kramer, M. S. Feld, Circulation 96 (1997), 99-105, which deals with the determination of human coronary artery composition by Raman spectroscopy in the fingerprint region.

In vivo application of Raman spectroscopy in most cases require the use of a flexible light guiding device of small diameter. This can for instance be introduced in the lumen of an artery. It must be able to reach and interrogate locations with atherosclerotic lesions. It can also be used in the working channel of an endoscope or inside a biopsy needle or biopsy forceps. The fiber optic probe (comprising one of more optical fibers) must guide light to the tissue under investigation, collect light that is scattered by the tissue and transport this collected light away from the tissue towards a spectrum analysis device.

Unfortunately, in the 400-2000 $cm^{-1}$ spectral region, the materials of the optical fiber itself generate Raman signal, resulting in a strong signal background. Moreover, bending of the fiber leads to variations in the amount of signal obtained from the core, cladding and coating materials, further complicating signal detection and signal analysis. This deteriorates the signal-to-noise with which the tissue Raman signal can be detected, and also otherwise complicates signal analysis, and therefore negatively affects clinical utility. It is therefore necessary to use optical filters at or near the distal end of the fiber optic probe which is in contact or in close proximity to the tissue, in order to suppress background signal contributions to the detected tissue Raman signal. However, this in turn necessitates the use of separate optical fibers for guiding laser light to the tissue and for collecting and guiding scattered light away from the tissue. It furthermore often necessitates the use of beam steering arrangements or a lens or lenses at the distal end of the fiber optic probe in order to obtain the desired overlap between the volume of tissue illuminated by the laser light and the volume of tissue from which Raman signal can be collected. Fiber optic probes for Raman spectroscopy are therefore complex. It is difficult to miniaturise fiber optic probes for Raman spectroscopy and to keep them flexible, which is necessary for instance for intravascular use and for use in the auxiliary channel of an endoscope. The complexity is also an obstacle to the production of such probes at a price that they can be used as disposables in hospitals. Moreover, signal intensity of tissue in the 400-2000 $cm^{-1}$ is low, necessitating relatively long signal integration times, which may be impractical for clinical use. All above mentioned problems and disadvantages hinder the actual implementation of Raman spectroscopy for clinical diagnostic purposes in general, and for intravascular use in particular.

Light is guided through the optical fiber in so-called bound modes. In these bound modes the electromagnetic field is located primarily in the core of the optical fiber, with a small part extending into the cladding. Lower order modes are more confined to the core than higher order modes.

The intensity of light that is guided by an optical fiber is attenuated. This is caused by absorption, by light scattering (Rayleigh scattering, scattering/reflection at larger inhomogeneities or at sites at which the fiber material is damaged), and by micro and macro-bending losses.

Laser light, that is lost by scattering events leaves the core of the fiber and passes through the coating (and buffer) layers. Coating and buffer layers are usually made of silicon or plastic or polymer material.

U.S. Pat. No. 5,293,872 teaches the use of near-infrared (NIR) laser light excited Raman spectroscopy for distinguishing between normal artery tissue, calcified atherosclerotic plaque and fibrous atherosclerotic plaque. For in vivo measurements in the 700-1900 $cm^{-1}$ region, the use of a bundle of optical fibers is discussed. This will lead to the same disadvantages as discussed above, e.g. with respect to noise.

U.S. Pat. No. 5,194,913 recognises the problem of multiple fiber optics, but also notes that the use of a single fiber is prohibited by the fact that background Raman signal generated in the fiber optics is intense for all but the shortest fibers. It discloses a fiber optic apparatus using two opposite fibers and using optical filters to reduce background Raman emission from the fiber optics. This document is related to the problem of signals in fibers in general, and it is clear that the solution provided by U.S. Pat. No. 5,194,913, i.e. an axial configuration, cannot easily be used for measurements in vivo.

A paper of J. F. Aust, K. S. Booksh and M. L. Myrick, Applied Spectroscopy 50 (1996), 382-386 discusses cases in which the signal obtained from the sample is relatively strong (polymer) or in which special measures were taken, such as increasing the measurement volume from which sample-Raman signal is obtained, to increase signal intensity from polymers to levels that are very much higher than would be obtained from a biological tissue. This paper does not discuss the applicability of the method to tissue, but teaches that for a good signal, a special Teflon tube of up to 4 cm has to be used on the tip of the optical probe, filled with the polymer, in order to get a good signal. Such a method is usually not applicable to tissue, especially not in the case of in vivo measurements.

Next to atherosclerosis, cancer is also an import health issue. The same problems as encountered above apply for determining tumor cells by Raman spectroscopy via fiber optics. U.S. Pat. No. 5,261,410 teaches to use a bundle of fibres and to measure in the fingerprint region. Such use also leads to a signal to noise ratio which is not satisfying.

From the above it is clear that there is a need for an cut for an instrument for measuring a Raman signal of a tissue, that does not have above mentioned problems.

SUMMARY OF INVENTION

The invention provides an instrument and the use of an instrument comprising a laser, a signal detection unit for measuring the Raman signal, and a fiber optic probe, wherein the fiber optic probe comprises one or more optical fibers for directing laser light onto the tissue and for collecting light that is scattered by the tissue and guiding the collected light away from the tissue towards the signal detection unit, the fiber comprising a core, a cladding and optionally a coating, and the fiber or fibers for collecting light having substantially no Raman signal in one or more parts of the 2500-3700 $cm^{-1}$ spectral region, and wherein the detection unit records the Raman signal scattered by the tissue in said spectral region.

BRIEF DESCRIPTION OF DRAWINGS

FIG. 9 schematically shows an embodiment in which Raman spectroscopy is combined with fluorescence and NIR-absorption spectroscopy.

DETAILED DESCRIPTION OF INVENTION

Figure 1A:
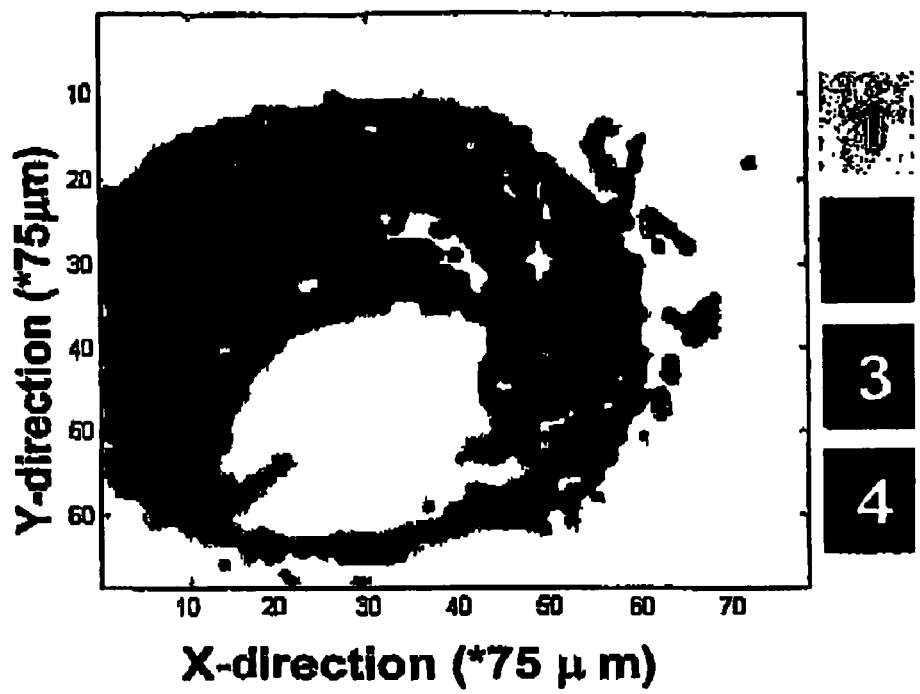
FIG. 1 shows the results of a Raman-mapping experiment (FIG. 1A) in which Raman spectra from a thin section of arterial tissue were obtained in the higher wavenumber region, enabling identification of tissue areas with different molecular composition, and the corresponding Raman spectra (FIG. 1B)

The invention is related to the use of an instrument comprising a laser, a signal detection unit for measuring the Raman signal, and a fiber optic probe, wherein the fiber optic probe comprises one or more optical fibers for directing laser light onto the tissue and for collecting light that is scattered by the tissue and guiding the collected light away from the tissue towards the signal detection unit, the fiber comprising a core, a cladding and optionally a coating, and the fiber or fibers for collecting light having substantially no Raman signal in one or more parts of the 2500-3700 $cm^{-1}$ spectral region, and wherein the detection unit records the Raman signal scattered by the tissue in said spectral region.

The advantage of using this apparatus is that rapid in vivo and ex vivo characterisation of tissue, and diseased tissue e.g. atherosclerotic plaque tumors, pre-cancerous tissue and benign tissue lesions with the Raman spectrometer is enabled and that the signal collection time needed to obtain a Raman spectrum with sufficient signal-to-noise ratio is decreased. A further advantage is that, because no extra means, like e.g. filters are needed that limit the spectral throughput of the light guides, Raman measurements can easily be combined with other informative techniques such as fluorescence measurements, near-infrared absorption measurements and optical imaging techniques, which could make use of the same light guides, using the light guides both for guiding light to the tissue as wall as collecting light from the tissue and guiding it back to respectively a fluorescence or a near-infrared detection unit or using separate light guides for this.

The invention described herein is based on the surprising finding that very detailed information about the composition and compositional heterogeneity of an atherosclerotic plaque could be obtained, brain tumor tissue could be distinguished from normal brain tissue and from skull tissue, and necrotic brain (tumor) tissue could be distinguished from vital tumor tissue by recording and analysing Raman spectral maps of thin tissue cross sections using only the 2500-3700 $cm^{-1}$ region of its Raman spectrum.

Before, the Raman finger print region was used to detect these kinds of tissue (see e.g. U.S. Pat. No. 5,293,812; U.S.

Pat. No. 5,261,410; Anal. Chem. 72 (2000), 3771-3775; Appl. Optics 26 (1987), 3175-3177; Circulation 96 (1997), 99-105), but it was not known or suggested that above mentioned tissue would also have characteristic and distinctive Raman signals in this higher wavenumber region. Selection of this region has large advantages. For measurements in the finger-print region of the Raman spectrum it is necessary to suppress the intensity of the elastically scattered laser light with special optical filters that combine a deep attenuation of the intensity of the elastically scattered laser light with a high transmission at wavelengths close to the laser wavelength. However, in the present invention a large wavelength shift exists between the incident laser light and the Raman-scattered light in the high wavenumber region. This enables the use of very simple and inexpensive absorption filters in the signal detection pathway for suppression of the intensity of elastically scattered laser light, such as e.g. a colour glass filter.

In general the intensity of the Raman signal of tissue is significantly higher (by a factor of about 5 or more) in this higher wavenumber region than in the 400-2000 $cm^{-1}$ region (fingerprint), enabling reduced signal collection times, e.g. also about by a factor of about 5 or more.

Another advantage of selecting this region is that this enables the recording of tissue Raman signal, using a single optical fiber to illuminate the tissue and to collect Raman signal from the tissue, with the tissue Raman signal being of comparable intensity or even higher intensity than that of the background signal generated in the optical fiber. Some fibers are very suitable for these kind of measurements, since the Raman scattering of the fiber itself in this wavelength region is low or negligible compared to the signal of the tissue. This is different from the fingerprint region where in the same configuration the signal background of the optical fiber, in practical situations, using a fiber of several meters in length, has an intensity that is usually more than an order of magnitude higher than the Raman signal of the tissue.

In addition, the background signal from some types of optical fiber in the 2500-3700 $cm^{-1}$ region consists of only a signal of which the intensity variations as a function of wavenumber shift are very small compared to that of the tissue Raman signal and therefore can be easily distinguished from the tissue Raman signal and/or accounted for in the signal analysis. In the fingerprint region the background signal from the fiber has sharper features making signal analysis harder. Hence, the signal-to-background ratio in the wavenumber region of the invention is much higher, than in the fingerprint region. This is due to the finding that the Raman signal of the fiber is absent or strongly diminished in the higher wavenumber region of the Raman spectrum, whereas in the fingerprint region, as used in the prior art, the fiber also generates a Raman signal, disturbing or even overcoming the Raman signal of tissue or sample.

Especially the 2700-3100 $cm^{-1}$ region of the Raman spectrum is informative for the above mentioned tissue. Therefore, in a preferred embodiment of the invention, the detection unit of the instrument records the Raman signal in one or more parts of the 2700-3100 $cm^{-1}$ spectral region. A further advantage therefore is that now, only signal in a small wavenumber region needs to be recorded, enabling the use of a multichannel light detector with fewer channels. Though the 2700-3100 $cm^{-1}$ spectral region is especially informative for detecting, analysis and diagnosis of diseases in tissue, preferably atherosclerotic plaque and cancerous or pre-cancerous tissue, the invention does not exclude measurements outside the mentioned spectral regions in order to obtain additional information. The invention also comprises in an embodiment collecting Raman signal in other spectral regions (e.g. the fingerprint region) in addition to the 2700-3100 $cm^{-1}$ spectral region.

An advantage of the use of the Raman generation and detection instrument is that the complexity of Raman spectrometers for measuring samples (especially (in vivo) tissue measurements), characterisation and/or tissue classification, is decreased by using the higher wavenumber spectral region and carefully selecting light guides that serve both to guide laser light to the tissue as well as to guide away light that is scattered by the tissue. Hence, the invention comprises the use of an instrument, wherein the fiber optic probe comprise an optical fiber that not only directs laser light onto the tissue but also both collects light that is scattered by the tissue and guides the collected light away from the tissue towards the signal detection unit. This embodiment also encompasses a fiber optic probe having a number of fibers that serve both to guide laser light to the tissue as well as to guide away light that is scattered by the tissue. Since one, a number, or all of such fibers in the probe can do this, the dimensions of the fiber optic probe can be diminished with respect to state of the art fiber optic probes for tissue characterization (which comprise different fibers for guiding laser light to the sample and detecting the Raman signal).

A further advantage is that the size of a Raman catheter for in vivo intravascular use can even be minimised to only one single optical fiber. This means that the diameter of e.g. the intravascular fiber optic probe can be maximally reduced and that maximal fiber optic probe flexibility can be achieved, which e so highly desirable attributes of catheters for intravascular use. Also for other applications, where small fiber optic probes are desirable, the instrument can be used.

A significant reduction of complexity and following from that a reduction of production cost of the fiber optic is another advantage. The fiber could even be used as a disposable, which is highly desirable for an intravascular catheter in clinical use.

In another embodiment of the invention, the Raman measurements can be combined with fluorescence and/or near-infrared absorption measurements. Hence, the detection unit will also comprise a detector for measuring fluorescence and/or a detector for near-infrared absorption. In this embodiment, it is e.g. possible that the fluorescence and/or near-infrared absorption measurements make use of a fiber also used in obtaining Raman signal.

In a further embodiment, only one single optical fiber is used for directing laser light (and (N)IR light) onto the tissue, as well as for collecting Raman signal that is scattered by the tissue, for collecting fluorescence and/or near-infrared signal, and for guiding the collected light away from the tissue towards the signal detection unit, which comprises the respective detectors.

In another embodiment, a plurality of fibers can be used to get an enhanced signal. This embodiment also comprises the use of an instrument wherein Raman measurements can be combined with fluorescence and/or near-infrared absorption measurements and wherein the detection unit also comprises a detector for measuring fluorescence and/or a detector for near-infrared absorption. In another embodiment, the dimensions of the probe can further be diminished, when fluorescence and/or near-infrared absorption measurements make use of a fiber also used in obtaining Raman signal. Here, 'a fiber' encompasses one or more fibers. Such bundles of fibers can be used for measuring and/or scanning a tissue area. The advantage is that measurement locations can be closer together than in state of the art fiber optic probes, raising the resolution.

The small diameter and high flexibility provide the best possibilities for combining the Raman probe with other sensing modalities (e.g. intravascular ultrasound for intravascular use, and incorporation in an endoscope for oncological applications) and for incorporation in instruments for obtaining tissue samples (such as a biopsy forceps or a an instrument for obtaining fine needle aspirates) or with treatment modalities (e.g. devices that use heat to coagulate tissue, such as tumor tissue, or surgical instruments), Hence, the invention also comprises an instrument wherein part of the fiber is integrated or combined with a catheter that provides additional information about the tissue or which comprises means to obtain tissue samples, means to treat tissue and/or means used in surgical procedures.

All these advantages allow a much simplified instrumentation. The instrument therefore enables ex vivo, in vitro and in vivo analysis and diagnosis of atherosclerotic plaque and detection of tumor tissue with great advantages over current state-of-the-art technology.

In the context o this invention, "tissue" refers to tissue of human, animal or plant origin, but in particular is meant human or animal tissue. Tissue includes a biological cell or cells, an organ, or part, of a human or animal body or a substance extracted from, or from a part of, the human or animal body and can e.g. be bone, blood or brain. Tissue samples can be measured, i.e. Raman signals can be measured, which are elicited by illumination with light emitted by the laser, in vitro or in vivo. Tissue is considered to belong to a particular clinical diagnostic class if it possesses one or more characteristic features, which may include but are not limited to, morphological, chemical, and genetic features. These can be typical of a certain pathological condition.

The fiber tip can be in or on the tissue, but can also be in close proximity, e.g. a few mm. However, the proximity can also be larger, when a lense is used to image the distal end of the fiber onto the tissue. In some cases, the tip cannot be on the sample, e.g. when the sample is measured through for example glass. In such a case, the proximity can even be a few centimeters or more. Proximity in this invention comprises both above-mentioned options.

The laser in this invention is any monochromatic light source with a line width sufficiently narrow to enable measurement of the desired Raman signal of a sample with sufficient spectral resolution, like a laser. The line width will in most cases preferably be below 5 $cm^{-1}$. The light beam of such a source is coupled into a fiber, and the light is shed on a sample. A Raman signal of such a sample may be produced by illuminating it with light from such laser source, provided that the sample contains molecules that have molecular vibrational modes that can participate in Raman scattering of incident light. Preferably for Raman measurements of tissue, the laser or source has an emission above about 600 nm, since in this way absorption of incident laser light in tissue is minimised and also autofluorescence of tissue is minimised. Autofluorescence can cause a background signal to the Raman spectrum which deteriorates the signal-to-noise with which the Raman signal is detected. Examples of sources are e.g. diode lasers, He—Ne lasers Ti-sapphire laser etc.

With "instrument" in the invention is meant a spectrometer comprising a combination of a laser, for producing a Raman signal, an optical fiber and a signal detection unit.

The spectrometer may comprise a filter to suppress the intensity of the component of the light that is guided to the spectrometer that has the same wavelength as the laser light. This filter should suppress the intensity of this light by preferably 8 orders of magnitude or more, while suppressing the intensity of the Raman scattering light in the wavenumber region of interest by preferably less than 10%. Because the higher wavenumber spectral region is used, implying a large wavelength interval between the laser light and the wavenumber region of interest, this may be a simple colour glass absorption filter, such as e.g. RG 780 colour glass file from Schott. Two of such filters in series and of 3 mm thickness (both commercially available) will suppress laser light below 725 nm by 10 orders of magnitude or more, while causing no significant attenuation of the Raman signal of interest other than reflection losses at glass air interfaces. Preferably, the entrance and exit faces of the filter are coated with an anti-reflection coating optimised for the wavelength region of interest, so as to minimise reflection losses at air-glass interfaces. In that way a throughput of Raman signal of more than 90% can easily be achieved. The spectrometer preferably has no moving parts, is optimised for throughput in the NIR, and has a resolution of preferably at least 8 $cm^{-1}$.

However, in some cases fluorescence might be desired (see above), as a source of information for characterisation of the tissue and to measure simultaneously or sequentially, either with one or with several fibers the Raman signal and fluorescence of the sample. In such an embodiment, the fluorescence excitation light may have wavelengths below 600 nm e.g. in the blue or UV.

The signal detection unit preferably comprises detectors like a multichannel CCD-detector optimised for light detection in the NIR. An example of such a detector is a deep-depletion back-illuminated CCD-camera (DU401-BRDD) from Andor-technology (Belfast, Northern-Ireland). The spectral region of interest can e.g. be chosen by a grating or prism. Recorded spectra are preferably displayed and/or analysed by means of dedicated software and a personal computer in real time.

In the context of this invention an optical fiber is defined as a device with a proximal end and a distal end, which is able to guide light from the proximal end to the distal end. The term "a fiber" comprises one or more fibers. The term "fiber optic probe" comprises one optical fiber or a bundle of optical fibers.

The distal end of the fiber probe may be shaped or be fitted with a micro-optical component physically attached to it, to arrive at certain illumination directions and/or angles and/or to arrive at certain light collection directions and/or angles and/or to determine the sample surface which is illuminated and/or to determine the size and/or location of the sample volume from which Raman signal is preferentially detected. In the art of measuring tissue with Raman spectroscopy, these probes usually contain one fiber for excitation and at least one fiber, but usually a number of fibers, to guide the (Raman) signal to a detector.

Optical fibers consist of a core and a cladding and usually one or more layers of protective coating. Such coating (comprising one or more coatings) can vary widely in thickness. The literature refers to the protective layer or layers surrounding the cladding of an optical fiber as "coating" or "buffer". In the context of this invention all single or multiple layers of material surrounding the cladding of an optical fiber are referred to as fiber coating. A jacket is sometimes applied to add further mechanical strength or to prevent too tight bending of the fiber. A jacket is defined as rigid or flexible tubing into which the optical fiber (or fibers) is inserted and which provides additional protection of the fiber (or fibers).

It was found that some fibers are very suitable for these kinds of measurements because the Raman scattering of the fiber itself in this wavelength region is low or negligible compared to the signal of the sample. Hence, the instrument comprises a fiber which has substantially no Raman signal in the spectral region where Raman signals are found.

In the context of the invention, "substantially" no signal, and similar phrases, means that such signal is of similar or smaller intensity than signal of tissue measured by the instrument, and distinguishable from signal of the tissue is distinguishable from other signal. For example, such signal is substantially absent, or e.g. an order of magnitude smaller.

An example of a preferred fibre is a fiber having a fused silica core and a fused silica cladding, like e.g. WF200/220A optical fiber from Ceramoptec Industries Inc. or FG-200-LCR fiber from 3M Company or equivalent fibers. Some fibers are less preferred, like e.g. WP200/220N optical fiber from Ceramoptec Industries Inc. or FT-200-EMR optical fiber from 3M Company, which appear to have a large background signal in the spectral region of interest.

Good results are obtained with optic fiber probes, wherein the fiber optic probe comprises at least one fiber with a low $OH^-$ fused silica core. Such an optical fiber contains very low amounts of $OH^{-1}$, whereby light absorption in the fiber in the near infrared region of the spectrum, which is the preferred spectral region for Raman measurements of tissue, is minimized. This may for example be a fiber optic probe, wherein the fiber optic probe comprises at least one optical fiber having a fused silica core and a fused silica or Teflon or TECS cladding (which have high transmission in the near-infrared), and wherein low background signal contributions are obtained from a coating, by using a coating material in which intrinsically little or substantially no signal is generated in the 2500-3700 $cm^{-1}$ wavenumber interval, or by applying measures to minimize generation and/or detection of coating signal, or both.

In a specific embodiment of the invention, the invention is directed to an instrument comprising a laser, a signal detection unit for measuring the Raman signal, and a fiber optic probe, wherein the fiber optic probe comprises one or more optical fibers for directing laser light onto the tissue and for collecting light that is scattered by the tissue and guiding the collected light away from the tissue towards the signal detection unit, and wherein an optical fiber comprise a core, a cladding and a coating, wherein the fiber or fibers for collecting light have substantially no Raman signal in one or more parts of the 2500-3700 $cm^{-1}$ spectral region, and wherein the detection unit records the Raman signal scattered by the tissue in said spectral region, and wherein the detection unit substantially does not measure Raman signal generated by other sources than the tissue. Such sources may be the fiber optic probe, e.g. the core, the cladding or the fiber coating of such fiber optic probe or of the optical fiber(s) therein. The phrase "does not measure Raman signal" means that the detection unit either does not receive such signal, or does not detect such signal, or both.

In a variation on this embodiment, the invention is directed is directed to an instrument comprising a laser, a signal detection unit for measuring the Raman signal, and a fiber optic probe, wherein the fiber optic probe comprises one or more optical fibers for directing laser light onto the tissue and for collecting light that is scattered by the tissue and guiding the collected light away from the tissue towards the signal detection unit, and wherein an optical fiber comprises a core, a cladding and a coating, wherein the fiber or fibers for collecting light have substantially no Raman signal in one or more parts of the 2500-3700 $cm^{-1}$ spectral region, and wherein the detection unit records the Raman signal scattered by the tissue in said spectral region, and wherein the detection unit substantially does not measure Raman signal generated by other sources than the tissue, and wherein the detection unit does substantially not measure fluorescence generated by other sources than the tissue. Herein, fluorescence may be e.g. fluorescence, e.g. by the core, cladding or coating material.

For example, polyimide coating (e.g. a applied in SFS200/210/233 RTF fiber, sold by Fiberguide Industries, Stirling, N.J., USA) has been found to lead to a strong fluorescence background, when compared to the Raman signal that is obtained from a tissue, when using a 720 nm laser light and an optical fiber with a length of 2 m.

Another example is WF200/220 P (from Ceramoptec), which is a fiber with a fused silica core, a fused silica cladding and a polyimide coating and which also shows a strong fluorescence background. For this reason polyimide coated fibers are less suitable for this invention.

In one embodiment, the feature that the detection unit substantially does not measure Raman signal generated by other sources than the tissue can e.g. be obtained by using a fiber or fibers for collecting light having substantially no Raman signal in one or more parts of the 2500-3700 $cm^{-1}$ spectral region. Examples of suitable core and cladding materials are fused silica and various forms of doped fused silica. Examples of unsuitable materials are ZBLAN (e.g. used in the fiber type Z100FJ, Z100FV, Z120AI sold by INO, Sainte-Foy, Quëbec, Canada) which shows relatively strong fluorescence when red or near-infrared laser light (e.g. 720 nm) travels through it, and plastic optical fibers, such as those made of PMMA (poly-methyl metacrylate) or polystyrene, and other which show a strong Raman signal in the high wavenumber region. Fibers consisting of fused silica core material and a Teflon cladding (such as the FLU-type fibers sold by Polymicro, Phoenix Ariz., USA) are suitable because, like fused silica, Teflon shows no Raman signal in the high wavenumber region. Sapphire based fiber is less suitable because of the chromium contamination that is usually present and which can give rise to luminescence in the red and near-infrared region of the spectrum. Such fibers need to be tested to determine if fluorescence of the fiber material is sufficiently low to enable good Raman spectra of tissues to be obtained.

Preferably, the coating material(s) that are applied to the cladding of the optical fiber, do not have a Raman signal in the high wavenumber region. Examples are embodiments the coating of the optical fiber comprises one or more of Teflon coatings and metal coatings (such as aluminum, copper or gold). Metal coated fibers are commercially available from e.g. Fiberguide Industries (Sterling, N.J., USA) and Oxford Electrics (Four Marks, United Kingdom).

The use of other coating materials than mentioned above is possible but generally requires extra measures, in order to minimize the intensity of background Raman signal that is generated in such coating materials. Such measures must minimize the amount of light that leaves bound fiber modes to enter and traverse the coating material, where coating Raman signal is generated and must ensure that only light that emerges from the core of the fiber and within the numerical aperture of the optical fiber reaches the Raman detector. Hence, in a further embodiment, the feature that the detection unit substantially does not measure Raman signal generated by other sources than the tissue can e.g. be obtained by using a detection unit, wherein the detection unit substantially measures only the signal obtainable from the core of the optic fiber.

For example, this may be achieved by using an instrument according to the invention, wherein laser light is coupled into the central part of the core of the optic probe (only), and under a numerical aperture that is as small as possible. In this way the laser light is primarily bound in low order modes of the fiber, which are the least lossy, and therefore lead to the least exposure of coating material to laser light and consequently the least generation of coating Raman signal.

In another embodiment, an instrument is used wherein the end face of the optical fiber, where the laser light is coupled into the optical fiber, is polished, to minimize surface imperfections, such that no microscopically visible surface imperfections remain. This can be achieved by application of generally known commercially available fiber polishing equipment. This minimizes scattering of laser light at the fiber end face surface in directions in which the laser light cannot be guided in a bound mode, and thereby minimizes exposure of the coating material to laser light.

In a further embodiment, a measure is to apply a second coating layer, wherein the fiber comprises a first and a second coating, the first coating as coating on the cladding and the second coating as coating on the first coating, wherein the second coating comprises a laser light absorbing material. In yet a further embodiment, the invention is directed to such second coating, wherein the fiber comprises a first and a second coating, the first coating as coating on the cladding and the second coating as coating on the first coating, wherein the second coating comprises a material having a higher refractive index than the first coating material, such as a combination of acrylate as first coating layer and black nylon as second coating layer (as applied in the AS200/220/IRAN fiber produced by FiberTech, Berlin, Germany). This measure suppresses multiple reflections of laser light at the interface between the first coating layer and air. Instead light primarily enters the second coating layer where it is absorbed. This limits the path length of laser light through coating material and thereby limits the amount of coating Raman signal that is generated.

A further measure is taking care not to subject the fiber to bending, especially not bending close to or below the minimal bending angle radius specified by the manufacturer. Bending causes light to leak out of the bound modes, which is a well known phenomenon, but or this invention with the additional adverse effect of generation of coating Raman signal. To achieve minimal bending of the fiber it can be inserted into a rigid or flexible tubing, e.g. stainless steel monocoil (Fiberguide Industries, Sterling, N.J., USA) which mechanically limits bending. The possibility to apply such tubing is dependent of course on potential restrictions dictated by the particular tissue characterization application.

Signal detection is best implemented in such a way that the signal detection unit substantially detects signal, which emerges from the core of the optical fiber and under an angle that is within a numerical aperture of the fiber. This can be accomplished by so-called spatial filtering, in which an imaging system is used to create an image of the fiber end face onto a diaphragm, before it is detected. The size of the diaphragm must be smaller or equal to the size of the image of the fiber core. In this way, only light that leaves the fiber end face through the core of the fiber will be transmitted through the diaphragm. A second diaphragm, which may be placed between the fiber end face and the first imaging element may be used to limit the numerical aperture of the imaging system to the numerical aperture of the optical fiber.

An alternative measure is to apply a mask over the fiber end face, which only leaves fiber core uncovered.

An addition measure is to remove the coating material near the fiber end face where laser light is coupled into the fiber over a length of about 5 mm or more, and to cover the cladding with black epoxy (e.g. Epotek, Billerica, Mass., USA). This will absorb any light traveling in the coating of the fiber in the direction of the signal detection unit, before it reaches the fiber end face. Hence, in an embodiment, the invention is also directed to an instrument and the use thereof, wherein the optical fiber comprises a laser light absorbing end tip coating, wherein the end tip is directed to the signal detection unit.

In a specific embodiment, the fiber can be connectorized (e.g. with an FC-connector) to couple the fiber to the glass in coupling optics and the signal detection optics. This enables an easy exchange of fibers without re-alignment of the system. The easy exchange of fibers as well as the low cost facilitates the application of fiber optic probes for high wavenumber Raman spectroscopic tissue characterization as a disposable. This has the advantage that a probe can be sterilized and packaged only to be unpacked immediately prior to application for tissue characterization. After the investigation the probe is discarded, by which any risk of insufficient resterilization before a next use is eliminated.

Due to Rayleigh scattering of laser light in the core and cladding material of the optical fiber, exposure of coating material to laser light cannot be completely prevented. The mechanisms described above, by which coating material becomes exposed to laser light, also enable a small fraction of the Raman signal that is generated in the coating material to enter into a guided mode of the fiber again, at which point it is no longer possible to avoid detection of this fiber background Raman signal along with the Raman signal of the tissue under investigation.

Therefore, in general, coating material in which no Raman signal can be generated in the high wavenumber region, such as in the metal coated fibers mentioned above, is preferred.

With some or all of the additional measures, which were described above, in place other coating materials can be used. For example, an instrument wherein the coating of the optical fiber comprises acrylate, Tefzel, TECS or silicone. In that way the fiber background Raman signal in acrylate coated fibers (such as AS200/220/IRAN fiber produced by FiberTec, Berlin, Germany, and AFS200/220 Y fiber sold by Fiberguide Industries, Sterling, N.J., USA) could be reduced below the level of detectability, using a laser emitting laser light with a wavelength of 720 nm and 100 mW of laser power, and a signal collection time of up to 10 seconds.

Such laser power and signal collection time are sufficient to obtain high quality high wavenumber Raman spectra of tissues, when the Raman signal emitted by the fiber optic is coupled into Raman spectrometer with a signal throughput 25% or higher, which are commercially available from a number of companies, and which employs a near-infrared optimized charge coupled device (CCD)-detector for Raman signal detection (such as a back-illuminated deep depletion CCD-camera available from And or Technologies, Belfast, UK).

Other non-limiting examples of suitable fibers are FG-200-LCR (which is a fiber with a fused silica core (200 micron in diameter), a fused silica cladding of 240 micron in diameter, a TECS coating of 260 micron in diameter and a Tefzel buffer of 400 microns in diameter), FT-200-EMT (also from 3M Company) which is an optical fiber with a cladding made of TECS, and WF 200/240 A, which is a fused silica core/fused silica cladding fiber with an acrylate coating (from Ceramoptec).

Silicone coated fiber is less preferable. Several silicone-coated fibers were tested Although silicone background signal can be reduced to a low level, some silicone background signal remains. This may limit applicability in applications which depend on very small differences in the Raman spectra of tissue. Examples of fibers that give rise to unfavourable background signal in the 2500-3700 $cm^{-1}$ spectral interval are WF 200/240 BN and WF200/240 BT, which are fused with a fused silica core and a fused silica cladding and a silicone buffer with a black nylon respectively a black Tefzel coating (Ceramoptec).

Hence, according to the invention, providing a fiber or fibers for collecting light having substantially no Raman signal in one or more parts of the 2500-3700 cm−1 spectral region, may be done with an instrument wherein the fiber optic probe comprises at least one fiber, or wherein the fiber optic probe comprises at least one optical fiber having a fused silica core and a fused silica or Teflon or TECS cladding, or by using a coating material in which intrinsically little or substantially no signal is generated in the 2500-3700 cm−1 wavenumber interval, or wherein the coating of the optical fiber comprises one or more of Teflon coatings and metal coatings, or wherein the detection unit substantially measures only the signal obtainable from the core of the optic fiber, or wherein the fiber comprises a first and a second coating, the first coating as coating on the cladding and the second coating as coating on the first coating, wherein the second coating comprises a laser light absorbing material, or wherein the fiber comprises a first and a second coating, the first coating as coating on the cladding and the second coating as coating on the first coating, wherein the second coating comprises a material having a higher refractive index than the first coating material, or wherein the optical fiber comprises a laser light absorbing end tip coating, wherein the optical fiber comprises a laser light absorbing end tip coating, or wherein the end face of the optical fiber, where the laser light is coupled into the optical fiber, is polished, or combinations thereof.

It is evident that the fiber has also sufficient transmission for the laser light and for the Raman signal of interest. A preferred fiber has a transmission for the wavelengths of the laser light and the Raman signal of at least 50%, and more preferably more than 90%. To increase light transmission preferably the proximal fiber end where laser light is coupled into the fiber is coated with an anti-reflection coating optimized for wavelength regions comprising the laser wavelength and the wavelengths at which Raman signal is measured.

The fiber optic probe may also comprise a bundle of fibers, wherein the fibers do not have a coating. The fibers may be closely packed in one fiber optic probe.

In another embodiment, the instrument is an instrument comprising an optical element at the distal end of the fiber optic probe for purposes of defining the location and/or volume of the sample which is illuminated and/or from which scattered light is collected.

With plaque or atherosclerotic plaque in this invention is meant a pathologic condition comprising a build up of fatty materials in the lining of an artery. It may be present in any artery of the body, most frequently in the coronary artery, the carotids, aorta, renal arteries, and distal arteries in the legs. Plaque or atherosclerotic plaque in and/or on tissue shows one or more characteristic Raman signals in the 2500-3700 cm$^{-1}$ spectral region. Such Raman signals are especially found around in the spectral region between 2700 and 3100 cm$^{-1}$.

In a preferred embodiment, the instrument comprises a fiber which has substantially no Raman signal in the spectral region where Raman signals are found which are characteristic to atherosclerotic plaque. Such Raman signals are especially found in the spectral region between 2700 and 3100 cm$^{-1}$. This also comprises an instrument, wherein the fiber has substantially no Raman signal in the spectral region where Raman signals are found which are characteristic to one or more of the group of lipid pools fibrous cap and/or the presence of macrophages or cholesterol therein. The positions of the Raman signals of these compounds can be derived by a person skilled in the art by comparing Raman spectra of tissue that is healthy and tissue that is affected and/or contains such compounds. With substantially "no Raman signal in one or more parts of a spectral region" is meant that the intensity of the detected background signal generated in the fiber is of the same order of magnitude as the Raman signal of the sample under investigation, or lower, in at least part of the spectral interval in which characterising Raman signal is found, and that the Raman signal(s) of the sample can be easily distinguished from this background signal. The instrument can measure in the complete spectral region between 2500-3700 cm$^{-1}$, preferably 2700 and 3100 cm$^{-1}$, but it is also possible to select part or parts of this spectral region for measurements and analysis and/or diagnosis.

In one embodiment, the instrument has a fiber which has substantially no Raman signal in the spectral region where Raman signals are found which are characteristic to cancerous tissue or pre-cancerous tissue, especially brain cancer. Such Raman signals are found in the 2500-3700 cm$^{-1}$ spectral region, especially in the spectral region between 2700 and 3100 cm$^{-1}$. With "cancerous tissue" is meant tissue that comprises cancer cells. Pre-cancerous tissue is to be understood as tissue that is abnormal tissue which is a pre-cursor of cancerous tissue.

Usually, in order to enable quick and/or automatic analysis, the instrument further comprises a signal analysis unit which analyses the recorded Raman signal. The analysis comprises an algorithm which outputs data regarding e.g. the molecular composition of the sample and/or the clinical diagnostic class to which the sample belongs.

Determination of the molecular composition of e.g. vascular wall or atherosclerotic plaque is accomplished by e.g. a least squares fit procedure in which the measured spectrum is fitted with a set of spectra of compounds known to be potentially present in the vascular wall or plaque. Quantitative information regarding molecular composition is then obtained from the fit coefficients. Alternatively, e.g. a partial least squares-algorithm may be developed that will accurately determine molecular composition. For detection of cancerous tissue various well known multivariate statistical analysis and/or neural network analysis methods can be employed, such as linear discriminant analysis and artificial neural networks. These analysis and/or diagnostic methods are known in the art, but the specific parameters will be adapted to the respective tissue or sample under investigation.

Such an instrument, comprising a signal analysis unit, is very suitable for use in the diagnosis of diseases, like atherosclerotic plaque and/or cancerous tissue or pre-cancerous tissue. The signal analysis unit can provide information about the molecular composition of normal and atherosclerotic blood vessel wall, the clinical diagnostic class of an atherosclerotic lesion, fibrous cap thickness, the presence of macrophages in the fibrous cap, the presence, size and/or composition of a lipid pool, the presence of cholesterol (esters), the presence of cancerous or pre-cancerous tissue, vital tumor or necrosis, and can provide specific signals for one or more of each.

The invention is also directed to the use of the Instrument for measuring a Raman signal of a tissue sample prior to it being resected, or biopted, or shortly after resection or biopsy, preferably excised, biopted or taken from a human or animal body. In another aspect, it is used for selecting tissue for biopsy or resection.

In another aspect of the invention, it comprises an instrument for measuring a Raman signal of tissue, the instrument comprising a laser, a signal detection unit for measuring the Raman signal, and a fiber optic probe, wherein the fiber optic probe comprises one or more optical fibers for directing laser light onto the tissue and for collecting light that is scattered by the tissue and guiding this collected light away from the tissue towards the signal detection unit, wherein the fiber of fibers for collecting light have substantially no Raman signal in one or more parts of the 2500-3700 cm$^{-1}$ spectral region, and wherein the detection unit is able to record the Raman signal scattered by the tissue.

In one embodiment, the fiber optic probe comprises an optical fiber that both directs laser light onto the tissue and collects light that is scattered by the tissue and guides this collected light away from the tissue towards the signal detection unit, and wherein the fiber has substantially no Raman signal in one or more parts of the 2500-3700 cm$^{-1}$ spectral region.

In a further aspect of the invention, it comprises a method for measuring a Raman signal of a tissue sample, wherein an instrument according to the invention is used and wherein the tissue sample is excised, biopted or taken from a human or animal body before measuring, or wherein a Raman spectrum is obtained of a tissue immediately after resection or biopsy.

The invention also comprises a method for producing and measuring a Raman signal comprising sending laser light through an optical fiber, receiving the Raman signal through an optical fiber and detecting the Raman signal by a signal detection unit, characterised by sending the laser light through a same optical fiber which also receives the Raman signal, using an optical fiber for this method which has substantially no Raman signal in one or more parts of the 2500-3700 cm$^{-1}$ spectral region, and wherein the signal detection unit measures the Raman signal in said spectral region. The end of said optical fiber, which is used to shed laser light on a sample, can be brought in, or in contact with, or in close proximity to said sample. Samples which are Raman active, will give a Raman signal, that can be detected via the same fiber which was used to produce the Raman signal.

In another embodiment, the invention is also directed to a method for producing and measuring a Raman signal of tissue, comprising providing a laser, a detection unit for measuring a Raman signal, and a fiber optic probe, wherein the fiber optic probe comprises one or more optical fibers for directing laser light onto the tissue and for collecting light that is scattered by the tissue and guiding the collected light away from the fiber toward the signal detection unit, the fiber comprising a core, a cladding and optionally a coating, sending laser light through the one or more optical fibers, receiving the Raman signal from the tissue through the one or more optical fibers and detecting the Raman signal by a signal detection unit, the fiber or fibers for collecting light having substantially no Raman signal in one or more parts of the 2500-3700 cm$^{-1}$ spectral region, and wherein the signal detection unit records the Raman signal in said spectral region. In a variation on this embodiment, the invention is directed to a method further comprising sending the laser light through a same optical fiber which also receives the Raman signal, using an optical fiber for this method which has substantially no Raman signal in one or more parts of the 2500-3700 cm$^{-1}$ spectral region.

In a specific embodiment, the above mentioned method is a method for analysing tissue by measuring a Raman signal, comprising sending laser light through one end of an optical fiber, bringing the other end of said optical fiber in, or in contact with, or in close proximity to the tissue of interest, receiving the Raman signal scattered by the sample through an optical fiber and detecting the Raman signal by a signal detection unit, characterised by sending the laser light through the same optical fiber which also receives the Raman signal, and using an optical fiber for this method which has substantially no Raman signal in one or more parts of the 2500-3700 cm$^{-1}$ spectral region. If necessary, e.g. to improve the signal to noise ratio, multiple Raman measurements of the tissue under investigation are made.

In another embodiment of the method of the invention, the signal of a detection unit is send to a signal analysis unit which analyses recorded Raman signal, the analysis unit comprising an algorithm which outputs data regarding the molecular composition of the sample and/or the clinical diagnostic class to which the sample belongs.

In order to analyse or make a diagnosis, several methods can be used to derive information. For example, the invention comprises a method, wherein prior to obtaining measurements of the tissue area of interest, measurements are made of tissues normally encountered in the area of interest. But it also comprises a method wherein prior to scanning the tissue area of interest, measurements are made of tissue or tissues affected by the specific disease to be detected in the tissue area of interest and in the same spectral region or a part or parts of this region. Hence, it comprises a method for evaluation of the Raman signal obtained from the tissue region of interest, in order to determine whether such Raman signal was obtained from normal tissue or from diseased tissue.

The invention is also directed to a method for evaluating the suitability of a type of fiber for measuring the Raman signal of tissue comprising:
  using an instrument according to the invention,
  performing a measurement without tissue being present at the distal end of the fiber,
  performing a measurement with tissue being present at the distal end of the fiber,
  comparing the spectra obtained with and without tissue being present
  concluding that the fiber is suitable for measuring the Raman signal of tissue.

A fiber is suitable, when Raman signal of tissue is distinguishable from Raman signal of the fiber (when such Raman signal of the fiber is present).

In another aspect of the invention, the invention is directed to a method for evaluating the suitability of a type of fiber for measuring the Raman signal of tissue, wherein a tissue sample is excised, biopted or taken from a human or animal body before measuring and wherein the Raman signal of the optical fiber is measured of the sample and of a blanc, and wherein the Raman signals of the sample and of the blanc are compared.

The method of the invention can be used for diagnosing human or animal blood vessel wall tissue, for diagnosing human or animal tissue on the presence of dysplasia, for determining the molecular composition of normal and atherosclerotic blood vessel wall, for determining the clinical diagnostic class of an atherosclerotic lesion, fibrous cap thickness, the presence of macrophages in the fibrous cap, the presence, size and/or composition of a lipid pool, the presence of cholesterol (esters), the presence of anomalous, cancerous or pre-cancerous tissue vital tumor or necrosis.

The method of the invention can also be used for evaluating the effect of medicaments, food or dietary food, or therapy on diseased or healthy tissue.

The method of the invention and the instrument of the invention can also be used for skin diagnosis, and skin classification, like objective skin classification. Significant differences exist between the high wavenumber Raman spectra of old skin, young skin and atopic skin. These differences are attributable to differences in the relative concentrations of protein, lipids and water. Fiber optic high wavenumber Raman spectroscopy therefore possesses the potential to discriminate in an objective way between different skin types and or skin conditions. This information is of value for the development and controlled testing of personal care products and topically applied pharmaceutical products, as well as the individual customer or patient optimized selection of such products, because different skin types may respond differently to such products or may require different formulations to obtain a desired effect.

In the invention, "light that is scattered by the tissue" refers to Raman scattering by the tissue. This does not exclude that the tissue also shows fluorescence, due to laser light excitation.

The results of the use of the instrument will generally not lead to a result that immedeatly enables a decision to be taken and/or a diagnosis to be concluded. Also the use and the method of the invention does not contain all steps which are required to diagnose, and will mainly or only provide interim results. Hence, diagnosis in this invention may mean analysis, which does not immedeatly enables a diagnosis, or analysis, which does immedeatly enables such diagnosis.

EXAMPLES

Example 1

Raman Mapping of Atherosclerotic Artery

This experiment describes the possibilities of Raman spectroscopy in the spectral region of the invention for studying artherosclerotic plaque.

The human coronary artery sample used to create the Raman map shown in FIG. 1 was obtained at the time of autopsy (less than 24 hour post mortem). It was snap frozen in liquid nitrogen and stored at −80° C. until use. For the Raman measurements a 20 µm thick cryosection was placed on a calcium fluoride ($CaF_2$) window (Crystan UK) and passively warmed to reach room temperature. After Raman measurements it was stained with a standard hematoxylin and eosin staining procedure.

To collect Raman specta, 719 nm laser light from an argon-ion pumped Titanium: Sapphire laser system (Spectra Physics, Mountain View, Calif.) was used. The Raman microspectrometer system that was used has been described in detail in Van de Poll S W E, Bak Schut T C, Van der Laarse A, Puppels G J "*In Situ Investigation of the Chemical Composition of Ceroid in Human atherosclerosis by Raman Spectroscopy*" J. Raman spectrosc. 33:544-551 (2002). A 80× NIR optimized objective (Olympus MIR-plan 80×/0.75, Japan) with a working distance of approximately 1.6 mm was used to focus the laser light onto the arterial section, and to collect light that was scattered by the tissue sample. For automatic scanning of the tissue sections, the microscope was equipped with a motorized, computer controlled sample stage. The pixel area was scanned through the laser focus in both lateral directions during each measurement, in order to obtain an average Raman spectrum of the entire pixel. Acquisition of Raman spectra and microscopic stage movement was controlled by Grams/32 Spectral Notebase Software (Galactic Industries Corp., Salem, N.H.). Laser power underneath the microscope objective was approximately 40 mW.

The $CaF_2$ window with the tissue was placed underneath the microscope. The computer controlled sample stage was moved over a two-dimensional grid, and Raman spectra were acquired with a collection time of 1 second per grid point. Wavenumber calibration of the spectra was performed using three known Raman calibration standard (4-acetamidophenol, (Sigma), naphthalene, cyclohexane (ICN Biochemicals)), and the emission lines of a neon and a neon-argon lamp. The spectra were corrected for cosmic rays and corrected for wavenumber dependent signal detection efficiency of the setup using a calibrated tungsten band lamp of a known temperature. Subsequently, the background signal, originating from the optical elements in the laser light delivery pathway was subtracted.

Raman Data Processing

For all data processing, Metlab 6.1 version R12 (Mathworks Inc., Natick, Mass.) was used.

K-means Cluster Analysis

Principal component analysis (PCA) followed by K-means clustering analysis (KCA) was used to determine the heterogeneity in Raman spectra within each tissue sample, in a non-subjective way and without assuming prior knowledge of the morphology and composition of the artery samples. This clustering analysis algorithm was used to find groups of spectra with similar spectral characteristics (clusters). In brief, the analysis was carried out on normalized first derivatives of the spectra (2700 to 3100 $cm^{-1}$) in order to diminish any influence of variations in the absolute intensity of the Raman signal and to correct for a slight slowly varying signal background due to slight antofluorescence from the tissue. First, PCA was performed on the Raman spectra, to orthogonalize and reduce the number of parameters needed to represent the variance in the spectral data set. The first 100 principal components were calculated, typically accounting for up to 99% of the signal variance. The PC scores, obtained for each spectrum, were used as input for KCA. The number of clusters in which the spectra are grouped by KCA is defined by the user. After KCA, a particular grey-tone was assigned to each cluster. Each grid element of the Raman map was then assigned the grey-tone of the particular cluster to which its spectrum belonged. In this way a grey-tones-image of the frozen section was created, in which areas with similar spectra had the same grey-tone. Finally, the averaged Raman spectrum of each cluster was calculated.

FIG. 1 shows the result of a Raman mapping experiment in which spectra were obtained of a thin tissue cross section of unfixed human atherosclerotic artery in a 2-dimensional grid of 80×70 points. The differences between spectra obtained from grid points with equal gray tone were smaller than between spectra obtained from grid points with different gray tone, as determined by a K-means cluster analysis of the data Tissue grid points with equal gray tone therefore have similar molecular composition. Tissue grid points with different gray tone show significant difference in molecular composition.

A) Result of a 4 clusters K-means clustering analysis. Cluster 1 coincides with adventitial fat. Cluster 2 coincides with artery wall. Clusters 3 and 4 coincide with an atherosclerotic lesion.

B) Cluster-averaged Raman spectra for clusters 1, 2, 3 and 4.

Figure 1B:
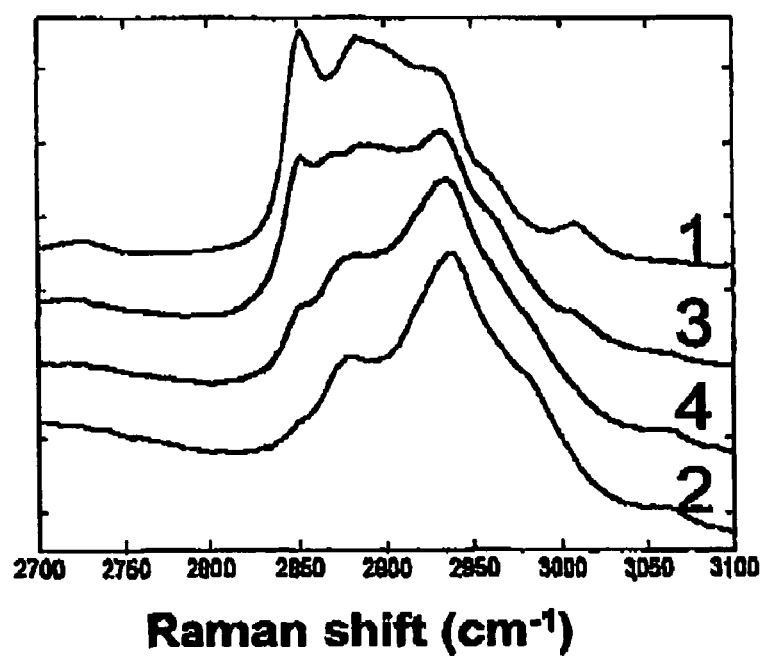

The differences in the spectra of FIG. 1B, as well as the highly structured localisation of tissue grid points with very similar spectra (belonging to a cluster) illustrate the sensitivity of high wavenumber Raman spectroscopy to the architecture of an atherosclerotic plaque in terms of its molecular composition. From the spectra information about the molecular composition of tissue grid points can be deduced by e.g. a classical least squares fitting procedure, in which tissue spectra are fitted with spectra of e.g. isolated compounds that can be present in the tissue.

Figure 2:
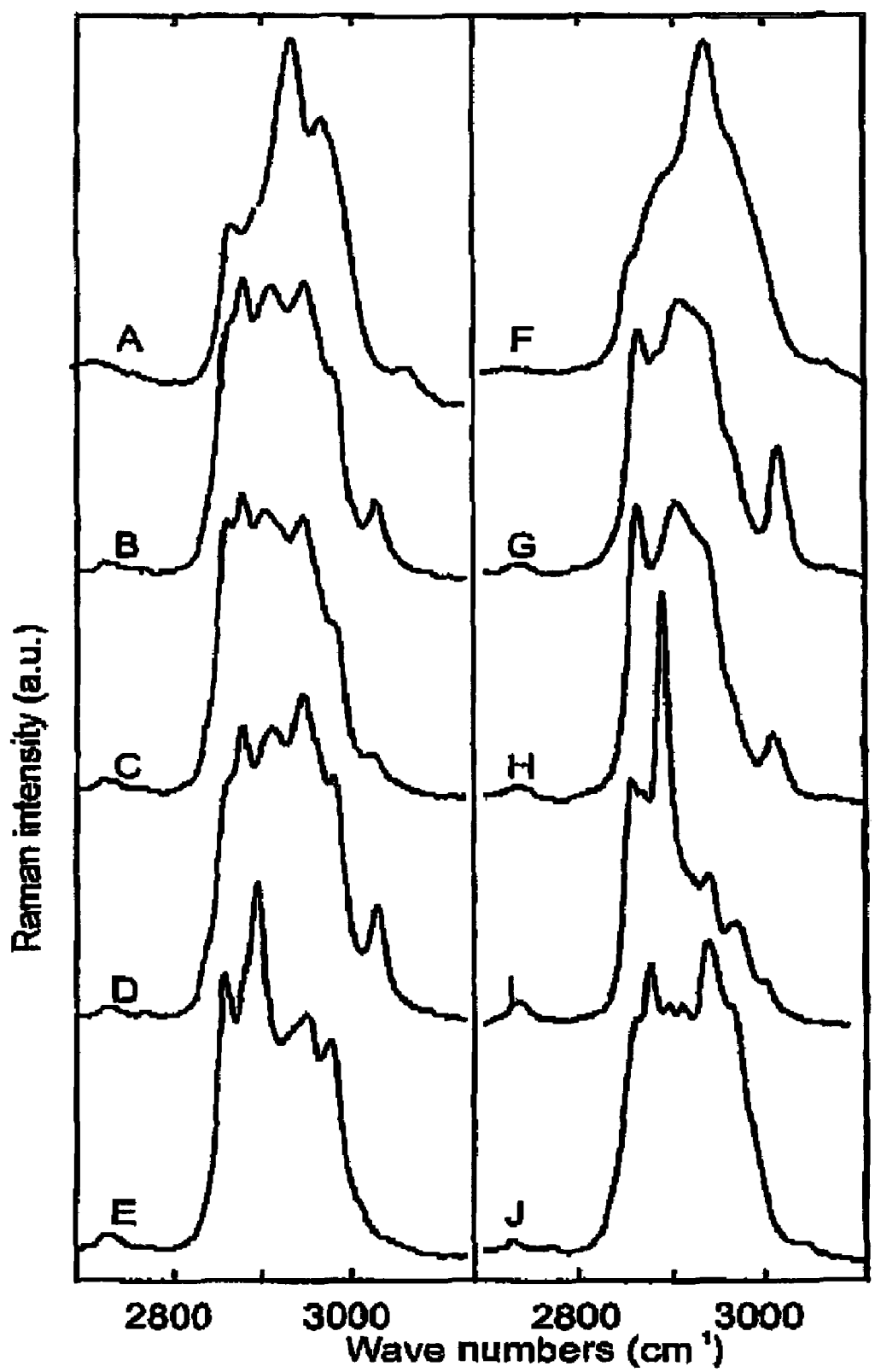
FIG. 2 shows spectra of lipids and proteins that can be present in atherosclerotic plaque and artery wall; A: elasitine, B: cholesteryl linoleate, C: cholesteryl oleate, D: cholesteryl linolenate, E: cholesteryl palmitate, F: collagen type 1, G: trilinoleine, H: triolene, I: Tripalmitine, J: cholesterol.

FIG. 2 shows spectra of such compounds: A: elastine, B: cholesteryl linoleate, C: cholesteryl oleate, D: cholesteryl linolenate, E: cholesteryl palmitate, F: collagen type 1, G:

trilinoleine, H: triolene, I: tripalmitine, J: cholesterol. This figure shows that these compounds, which can be present in artherosclerotic plaque and artery wall, have distinctive Raman signals in the spectral region of interest. Raman spectra of these chemicals were recorded using the same Raman setup as used for the measurements shown in FIG. 1.

Table 1 shows the result of a least squares fit of cluster averaged spectra 1-4 of FIG. 1B with the pure compound spectra of FIG. 2 and a 1st order polynomial to account for a slightly sloping background. Cluster averaged Raman spectra were fitted with the set of Raman spectra of spectra of these pure compounds, using a non-negative (which means that only positive fit-coefficients are allowed) linear least squares fitting routine. The first order polynomial was included in the fit to account for a slight (fluorescent) background in the Raman spectra. The sum of the non-negative least squares fit contributions of the compound spectra was set to 100%.

The percentages shown relate to the relative signal contributions of the protein, cholesterol, triglyceride and cholesterol ester spectra shown in FIG. 2. Signal contributions of different cholesterol esters were co-added ("total cholesterol esters" in table 1), signal contributions of different triglycerides were co-added ("total triglycerides") as well as those of collagen and elastin ("total proteins").

TABLE 1

Relative signal contributions of cholesterol, cholesterol-esters, triglycerides and proteins signal obtained from different regions of an artery wall containing an atherosclerotic lesion.

| Cluster | Location | Cholesterol | Total cholesterol esters | Total triglycerides | Total protein |
|---|---|---|---|---|---|
| 1 | adventitial fat | 0% | 11% | 88% | 1% |
| 2 | Normal artery wall | 2% | 0% | 0% | 98% |
| 3 | Atherosclerotic lesion | 14% | 33% | 29% | 24% |
| 4 | artery wall surrounding lesion | 2% | 21% | 3% | 73% |

Figure 3:
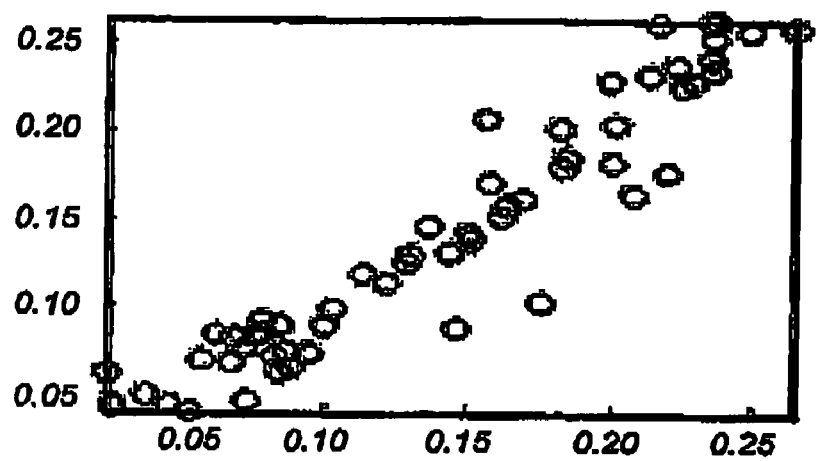
FIG. 3 provides a comparison of the lipid composition of segments of human arteries as determined by Raman spectroscopy and HPTLC (High Performance Thin Layer Chromatography).
Figure 3:
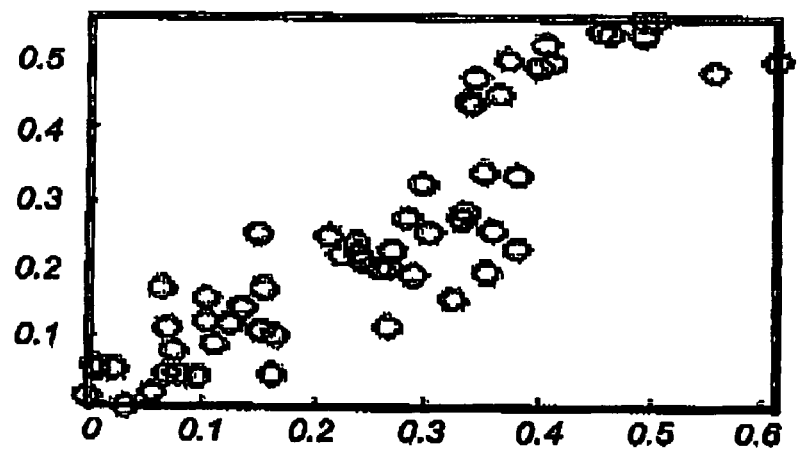
Figure 3:
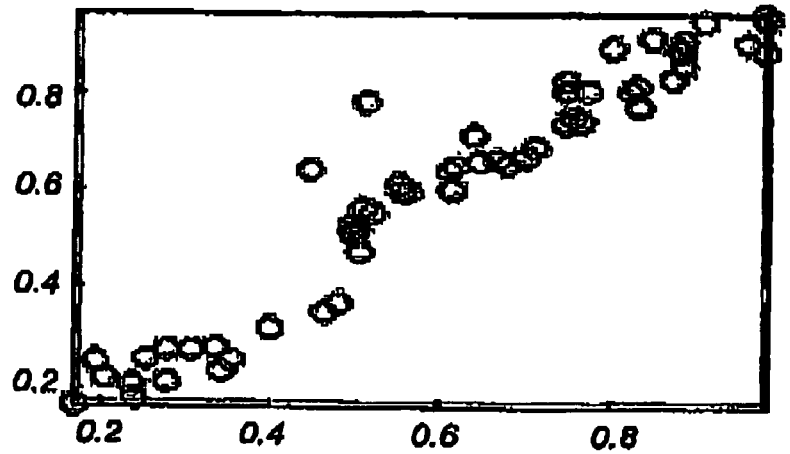

FIG. 3 shows the result of a comparison of the lipid composition of human arterial segments as determined by Raman spectroscopy and by HPTLC (high-performance thin-layer chromotography)). 58 arterial sequences of ~1 cm$^2$ were scanned under a Raman microspectrometer while Raman signal was collected in the higher wavenumber region (same instrument as for FIGS. 1 & 2). After the Raman measurements, lipids were extracted from the arterial segments and analysed by means of HPTLC. Total lipid fraction was normalised to 100%. A partial least squares analysis model was developed based on Raman and HPTLC results of 57 segments and applied to the Raman spectrum 58th segment to predict its lipid composition. The outcome was compared with the HPTLC analysis of the 58th segment. This leave one out evaluation was repeated for each of the 58 segments. FIG. 3 shows a comparison of the higher wavenumber Raman method for lipid composition determination in human arteries (in situ) and HPTLC for relative weight fractions cholesterol, total cholesterol esters and total triglycerides. High correlation coefficients were obtained (r=0.95 for cholesterol, r=0.93 for cholesteryl esters, r=0.96 for tryglycerides).

This experiment shows that Raman measurements in the spectral region of the invention give very good results and comparable information to HPTLC, enabling Raman spectroscopy as in vivo technique for studying artherosclerotic plaque Example 2

Raman Mapping of Cancerous Tissue

This experiment describes the possibilities of Raman spectroscopy in the spectral region of the invention for studying cancerous tissue.

Figure 4A:
FIG. 4 shows the results of a Raman-mapping experiment in which Raman spectra from a thin section of human dura, infiltrated by meningioma (MG), were obtained in the higher wavenumber region, enabling discrimination between these tissues (FIG. 4A) and an adjacent H&E (hematoxylin and eosin) stained section (FIG. 4B).
Figure 4B:

The high wavenumber region can also be used advantageously in various clinical oncology applications. For instance, FIG. 4A shows a Raman map obtained of a thin tissue section of human dura infiltrated by meningioma in a way similar to the map of an atherosclerotic lesion in FIG. 1A. Currently no good intra-operative assessment of excision margins is possible. However, it is known that meningioma tissue that is left behind may lead to recurrence of the tumor. FIG. 4B shows a picture of an adjacent tissue section after staining with hematoxylin and eosin (H&E stained). Surprisingly, the histopathological evaluation of this section and its comparison with the Raman map show that the light gray areas in the Raman map correspond to dura, while the dark areas correspond to meningioma (MG).

This experiment shows that Raman measurements in the spectral region of the invention give valuable information on cancerous tissue of the brain, enabling Raman spectroscopy as in vivo technique for studying such tissue.

Example 3

Raman Mapping of Cancerous Tissue

This experiments describes the possibilities of Raman spectroscopy in the spectral region of the invention for studying cancerous tissue.

Figure 5A:
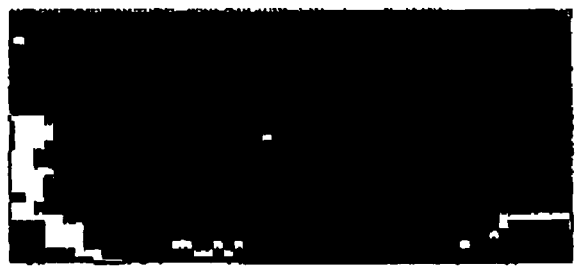
FIG. 5 shows the results of a Raman-mapping experiment (5A) in which Raman spectra form a thin section of human glioblastoma, were obtained in the higher wavenumber region, enabling identification of areas of vital tumor (V) and of areas of necrosis (N), when compared to FIG. 5B, where an adjacent H&E stained section is shown.
Figure 5B:

FIG. 5A shows a Raman map of a thin section of human glioblastoma with both vital tumor areas and areas with necrotic tissue. Surprisingly, comparison of the Raman map with the H&E stained adjacent section evaluated by a neuropathologist, shows that the light gray area corresponds to vital tumor tissue while the dark gray area in the Raman map corresponds to necrosis.

This experiment shows that Raman measurements in the spectral region of the invention give valuable information on cancerous tissue of the brain, enabling Raman spectroscopy for discriminating between vital tumor tissue and necrosis.

Example 4

Schematic Representation of Raman Spectrometer

Figure 6:
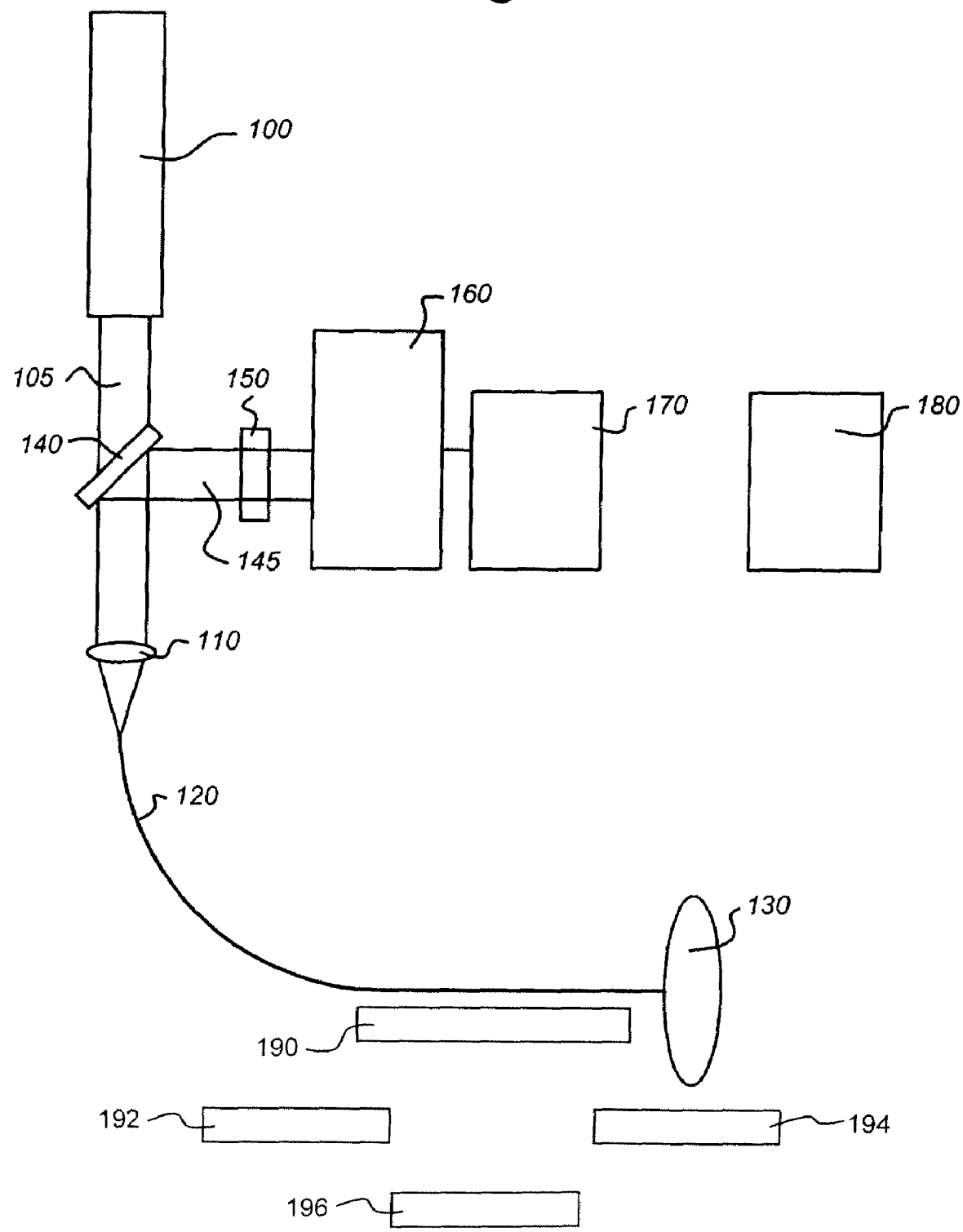
FIG. 6 schematically shows a set-up for obtaining Raman spectra in the higher wavenumber region.

FIG. 6 schematically shows a characteristic Raman measurement and analysis set-up comprising a laser 100, coupling optics 110, by which laser light following a first light path 105 is coupled into a fiber optic probe 120, which guides the laser light to the tissue 130 under investigation and which collects light scattered by the tissue and guides it back to coupling optics 110, a filter 140 which creates a light path 145 for Raman scattered light from the tissue 130, which is shifted in wavelength with respect to laser light from laser 100, a filter 150 for strong attenuation of remaining light of the same wavelength as the laser light in light path 145, a measuring unit 160, which measures intensities of the Raman scattered light at a plurality of wavelengths, a signal storage device 170 which may be electronically linked to measuring unit 160 and which stores measured intensities, and a signal analysis device 180, which may or may not be physically linked to signal storage device 170 or which may coincide with signal storage device 170, and which analyses the measured signals for instance to provide information about the molecular composition of the tissue 130 or to enable classification of the tissue, e.g. determination of the clinical diagnostic class to which the tissue belongs. The system can comprise a unit that gives an audible or visible signal when certain tissue is encountered. The invention is not limited to this configuration; the person skilled in the art can vary and/or choose the components which are according to his knowledge desirable or necessary.

If desired, the instrument part of the fiber of fiber optic probe 120 can be integrated or combined with a catheter 190 that provides additional information about the tissue or which comprises means 192 to obtain tissue samples, means 194 to treat tissue and/or means 196 used in surgical procedures.

Example 5

Steps to Arrive at a Tissue Analysis

This experiment describes the steps to arrive at a tissue analysis using high wavenumber-Raman spectroscopy The steps may be implemented in various ways (the description of the steps below, are therefore given by way of example and are not meant to be limiting in any way):
1) Tissue is illuminated through an optical fiber and light which is scattered by the tissue is collected by the same optical fiber.
2) The Raman spectrum of the collected light is recorded in the form of signal intensities vs. detector channel number.
3) The measured spectrum is pre-processed prior to final analysis, this pre-processing step may comprise wavenumber calibration of detector channels, correction for varying wavenumber-dependent signal detection efficiency, correction of measured spectra for background signal contributions, generated anywhere in the Raman measurement system, but not due to the tissue under investigation.
4) Analysis of the pre-processed spectra. As an example a classical least squares analysis may be used in which the measured spectrum is fitted with spectra of compounds of which it is known that they may be present in the tissue in amounts sufficient to have a detectable contribution to the overall tissue spectrum and e.g. a polynomial with coefficients that can also be fitted to optimally take account of slowly varying backgrounds to the Raman spectrum that may be due to e.g. fluorescence excited within the sample. When the compound-specta are intensity-scaled prior to fitting the tissue spectrum, in such a way that the fit-coefficients for compound-spectra resulting from a fit of a spectrum of a sample containing equal amounts of these would be equal, then, apart from the fact that in practice different efficiencies may apply for collection of signal from different tissue volumes and that the tissue may be heterogeneous in molecular composition, values of the fit-coefficients are directly related to the weight-percentages of the respective compounds present in the tissue on condition that the tissue is sufficiently homogeneous. If this is not the case, the composition as determined will still be in qualitative agreement but not necessarily in quantitative agreement with the real composition. For instance, because the arterial wall and atherosclerotic plaque are not homogeneous in molecular composition, and because depending on probe geometry, Raman signal is collected with different efficiencies from different tissue volumes, and because of signal attenuation within the tissue, certain tissue volumes, with potentially different molecular composition, will contribute signal more effectively than others. The weight percentages of compounds present in the tissue may represent the actual information sought, or they may be used to type the tissue and determine its clinical diagnostic class. Alternative approaches for determining weight percentages of specific compounds or groups of compounds include the well known partial least squares analysis. Also other multivariate statistical signal analysis approaches such as principal components analysis, linear discriminant analysis, logistic regression analysis, or e.g. analysis based on an artificial neural network may be applied for determining the clinical diagnostic class of a tissue.
5) Outputting the desired data in a visible or audible form as well as storing the data with proper references for future assessment and/or cross-referencing with other data, such as e.g. coordinates of the location of measurement, or images of the location where the Raman spectrum was measured, e.g. an angiogram or intravascular ultrasound images.

Example 6

Lipid Measurements

Figure 7:
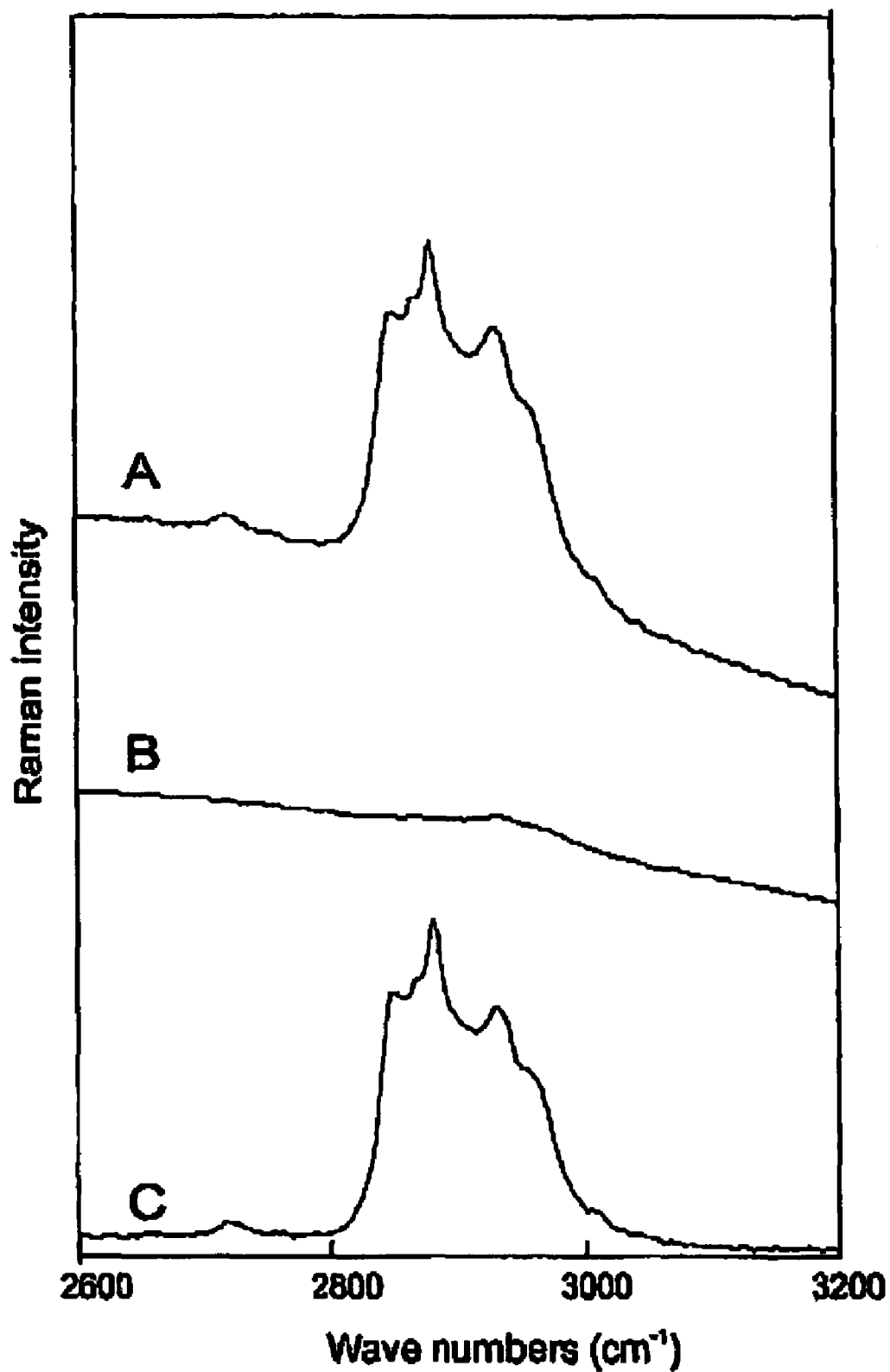
FIG. 7 shows a shows a spectrum (A) of a mixture of lipids measured with a Raman setup according to FIG. 6. Also shown are the spectrum of the fiber optic probe itself (B, obtained without a sample present at the distal end of the optical fiber) and a difference spectrum C (A-B).

FIG. 7 show a (A) of a mixture of lipids measured with a Raman setup according to FIG. 6. Specifically, the laser 100 was a ti-Sapphire-laser (model 3900S, Spectra Physics, USA) emitting laser light at 720 nm. Filter 140 was a custom made dielectric filter (produced by-Omitec, UK) which transmitted laser light of 720 nm and which reflected light returned from the sample with a wavelength above 850 nm. The direction of the incoming laser light and the normal to the filter surface included an angle of 15 degrees. Lens 110 was a microscope objective for use in the near-infrared (×20 PL-FL Nachet, numerical aperature 0.35). The optical fiber 120 was a WF200/220A optical fiber from Ceramoptec. The filter 150 was a color glass filter RG 780 (Schott). Light transmitted by filter 150 was imaged onto a an optical fiber with a core of 1000 microns which was connected to a round bundel of 64 optical fibers with a core diameter of 100 microns. At the distal end of this bundle the fibers were arranged in a linear array and light was guided into spectrometer 160 in this way. Spectrometer 160 was a Renishaw system RA 100 imaging spectrometer equipped with a deep-depletion CCD-camera for multichannel signal detection. Also shown are the spectrum of the fiber optic probe itself (B, obtained without a sample present at the distal end of the optical fiber) and a different spectrum A-B, illustrating that with a single properly selected unfiltered optical fiber, high quality spectra can be obtained of samples of similar molecular composition as may be encountered in atherosclerotic lesions.

FIG. 8 shows Raman spectra (t) of a normal artery wall (A) and an atherosclerotic artery wall (B), of the results (f) of a least squares fitting of these spectra with the set of spectra of purified compounds shown in FIG. 2 and of residuals (r) which represent the signal contained in the tissue spectra that is not accounted for by the set of fit-spectra. As can be seen by the low intensity of the fit-residuals, the fit of the tissue spectra is highly accurate enabling detailed information regarding molecular composition of the tissues to be obtained. This result is shown by way of example. For instance, the set of compound spectra which is used to fit the tissue spectra, may be composed of other spectra or a different number of spectra.

Figure 8A:
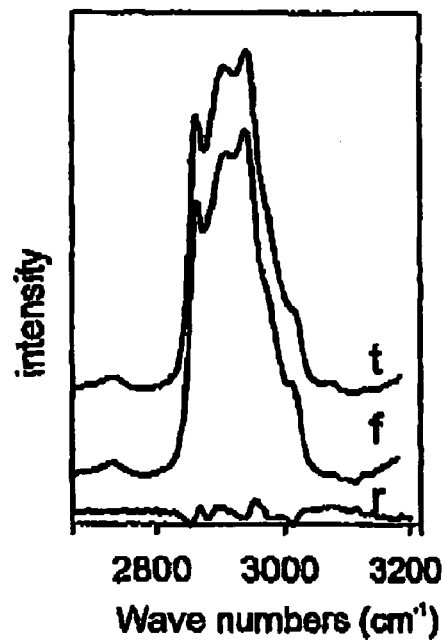
FIG. 8 shows Raman spectra (t) of a normal artery wall (A) and an atherosclerotic artery wall (B), of the results (f) of a least squares fitting of theses spectra with the set of spectra of purified compounds shown in FIG. 2 and of residuals (r) which represent the signal contained in the tissue spectra that is not accounted for by the set of fit-spectra.
Figure 8B:
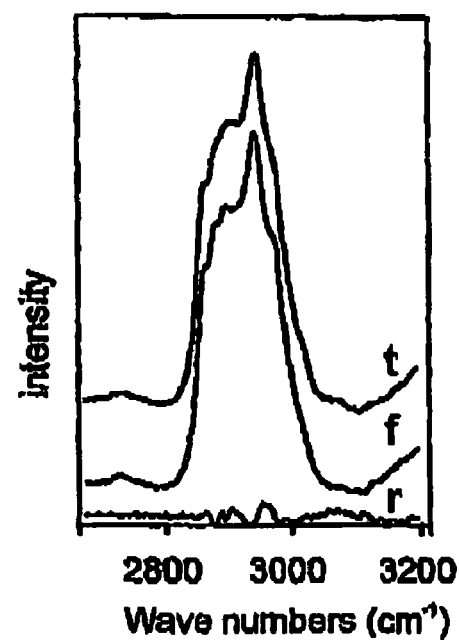

Table 2 shows a table with weight percentages of compounds or compound groups of the arterial samples of which the spectra are shown in FIGS. 8A and 8B, as determined from the results of the least squares fit analysis. The spectrum of the normal artery is dominated by signal contributions of triglycerides, representing the adventitial fat signal contributions, no or very minor signal contributions from cholesterol and cholesterol esters are found, in contrast with the signal obtained from the atherosclerotic artery which contains significant signal contributions from cholesterol and cholesterol esters.

TABLE 2 weight fractions of compounds or compound groups of the arterial samples of which the spectra are shown in FIGS. 8A and 8B

|  | Normal artery | Atherosclerotic artery |
|---|---|---|
| Cholesterol linoleate | 0.0078 | 0.3776 |
| Cholesteryl oleate | 0 | 0.0532 |
| Cholesteryl linolenate | 0.02 | 0 |
| Cholesteryl palmitate | 0.0187 | 0.1155 |
| Trilinoleine | 0.0477 | 0.0235 |
| Triolene | 0.7937 | 0.1436 |
| Tripalmitine | 0.0032 | 0 |
| Cholesterol | 0 | 0.1530 |
| Collagene | 0.0633 | 0.0756 |
| Elastine | 0.0456 | 0.0574 |

This experiment shows that spectrometer of the invention enables Raman spectroscopy as in vivo technique for studying artherosclerotic plaque, but now with the above mentioned benefits of this spectrometer.

Example 7

Instrument with Fibers Measuring Fluorescence and or NIR Absorption

FIG. 9 shows schematically an embodiment in which Raman spectroscopy is combined with fluroscence and NIR-absorption spectroscopy. This embodiment shows one single fiber on the left side of the figure and excitation light that is coupled via reflectors into the fiber. The same or another reflector is used to decouple from the obtained signal out of the fiber the fluorescence light for detection. Further to the right another reflector couples laser light into the fiber for producing a Raman signal from a sample. The same or another reflector is used to decouple the Raman signal out of the fiber to a detector. On the right hand side of the figure, NIR light of a NIR source is coupled into the fiber, and the NIR signal that is guided back by the same fiber is measure by a suitable detector. Measurements can be done sequentially or simultaneously. The fiber shown can also be a bundle of fibers. The person skilled in the art win adapt the optics sources, detection units etc. to his purpose, the tissue to be measured or the information that is desired.

Whilst specific embodiments of the invention have been described above, it will be appreciated that the invention may be practiced otherwise than as described. For example, the instrument can also be used to measure biological molecues, like lipids, etc. in other species than tissue, e.g. for use in the analysis of milk, oil, etc. The description and the examples are not intended to limit the invention.

The invention claimed is:

1. An instrument for measuring a Raman signal of tissue, the instrument comprising a laser, a signal detection unit for measuring the Raman signal, and a fiber optic probe, wherein the fiber optic probe comprises one or more optical fibers for directing laser light onto the tissue and for collecting light that is scattered by the tissue and guiding the collected light away from the tissue towards the signal detection unit, the fiber or fibers comprising a core, a cladding and optionally a coating, and the fiber or fibers for collecting light having substantially no Raman signal in one or more parts of the 2500-3700 cm$^{-1}$ spectral region, and wherein the detection unit records the Raman signal scattered by the tissue in said spectral region, the instrument further comprising a signal analysis unit which analyses the recorded Raman signal in one or more parts of the 2500-3700 cm$^{-1}$ spectral region, the analysis comprising an algorithm which outputs data regarding the molecular composition of the tissue and/or the clinical diagnostic class to which the tissue belongs.

2. Instrument according to claim 1, wherein the fiber optic probe comprises an optical fiber that both directs laser light onto the tissue and collects light that is scattered by the tissue and guides the collected light away from the tissue towards the signal detection unit.

3. Instrument according to claim 1, wherein the fiber optic probe comprises at least one fiber having a low OH— fused silica core.

4. Instrument according to claim 1, wherein the fiber optic probe comprises at least one optical fiber having a fused silica core and a fused silica or Teflon or TECS cladding.

5. Instrument according to claim 1, comprising a coating material in which intrinsically little or substantially no signal is generated in the 2500-3700 cm$^{-1}$ wavenumber interval.

6. Instrument according to claim 1, wherein the detection unit also comprises a detector for measuring fluorescence and/or a detector for near-infrared absorption.

7. Instrument according to claim 6 wherein fluorescence and/or near-infrared absorption measurements make use of a fiber also used in obtaining Raman signal and wherein the detection unit also comprises a detector for measuring fluorescence and/or a detector for near-infrared absorption.

8. Instrument according to claim 1 wherein the fiber optic probe comprises a bundle of fibers for measuring and/or scanning a tissue area.

9. Instrument according to claim 1, wherein part of the fiber is integrated or combined with a catheter that provides additional information about the tissue or which comprises means to obtain tissue samples, means to treat tissue and/or means used in surgical procedures.

10. Instrument according to claim 1, wherein the fiber optic probe comprises one single optical fiber.

11. A method for measuring a Raman signal of tissue employing an instrument comprising a laser, a signal detection unit, a signal analysis unit, and a fiber optic probe, wherein the fiber optic probe comprises one or more optical fibers, the method comprising using the fiber optic probe for directing laser light onto the tissue, collecting light that is scattered by the tissue and guiding the collected light away from the tissue towards the signal detection unit, the fiber or fibers of the fiber optic probe comprising a core, a cladding and optionally a coating, and the fiber or fibers for collecting light having substantially no Raman signal in one or more parts of the 2500-3700 cm$^{-1}$ spectral region, recording the Raman signal scattered by the tissue in said spectral region using the detection unit, using the signal analysis unit to analyze the recorded Raman signal in one or more parts of the 2500-3700 cm$^{-1}$ spectral region, and using an algorithm to output data regarding the molecular composition of the tissue and/or the clinical diagnostic class to which the tissue belongs.

12. Method according to claim 11, wherein the tissue is excised, biopsied or taken from a human or animal body before measuring.

13. Method according to claim 11, comprising measuring a Raman signal of a tissue sample prior to resecting or biopsying the tissue sample or for selecting tissue for biopsy or resection.

14. A method for producing and measuring a Raman signal of tissue, comprising providing a laser, a signal detection unit for measuring a Raman signal, and a fiber optic probe, wherein the fiber optic probe comprises one or more optical fibers for directing laser light onto the tissue to produce a Raman signal, for collecting light that is scattered by the tissue and for guiding the collected light away from the tissue toward the signal detection unit, the fiber or fibers comprising a core, a cladding and optionally a coating, the method comprising sending laser light through the one or more optical fibers, receiving the Raman signal from the tissue through the one or more optical fibers, detecting the Raman signal by the signal detection unit, the fiber or fibers used for collecting light having substantially no Raman signal in one or more parts of the 2500-3700 $cm^{-1}$ spectral region, and wherein the signal detection unit records the Raman signal in said spectral region, the method further comprising using the signal analysis unit to analyze the recorded Raman signal in one or more parts of the 2500-3700 $cm^{-1}$ spectral region using an algorithm and outputting data regarding the molecular composition of the tissue and/or the clinical diagnostic class to which the tissue belongs.

15. Method for evaluating an optical fiber for measuring a Raman signal of tissue, wherein an instrument according to claim 1 is used and wherein a tissue sample is excised, biopsied or taken from a human or animal body before measuring, and wherein the Raman signal of the optical fiber is measured of the sample and of a blank, and wherein the Raman signals of the sample and of the blanc are compared.

16. Method for evaluating the suitability of a type of fiber for measuring the Raman signal of tissue, comprising:
using an instrument according to claim 1
performing a measurement without tissue being present at the distal end of the fiber,
performing a measurement with tissue being present at the distal end of the fiber,
comparing the spectra obtained with and without tissue being present
concluding that the fiber is suitable for measuring the Raman signal of tissue.

* * * * *